United States Patent [19]

Law et al.

[11] Patent Number: 5,160,527

[45] Date of Patent: Nov. 3, 1992

[54] STABILIZED METAL SALT/3-ISOTHIAZOLONE COMBINATIONS

[75] Inventors: Andrew B. Law, Newtown; Gary L. Willingham, Glenside, both of Pa.

[73] Assignee: Rohm and Haas Company, Philadelphia, Pa.

[21] Appl. No.: 708,004

[22] Filed: May 24, 1991

[51] Int. Cl.$^5$ .......................................... C10M 105/30
[52] U.S. Cl. ...................................... 71/67; 514/372; 548/101; 548/213; 252/34
[58] Field of Search ................. 252/34, 327; 548/101, 548/213; 514/372; 71/67

[56] References Cited

U.S. PATENT DOCUMENTS

| | | | |
|---|---|---|---|
| 3,523,121 | 8/1970 | Lewis et al. | 260/306.7 |
| 3,761,488 | 9/1973 | Lewis et al. | 260/302 |
| 3,870,795 | 3/1975 | Miller et al. | 424/270 |
| 4,067,878 | 1/1978 | Miller et al. | 260/302 |
| 4,129,448 | 12/1978 | Greenfield et al. | 106/15 |
| 4,150,026 | 4/1979 | Miller et al. | 260/299 |
| 4,165,318 | 8/1979 | Greenfield et al. | 260/302 |
| 4,241,214 | 12/1980 | Miller et al. | 548/101 |
| 4,608,183 | 8/1986 | Rossmoore | 252/36 |
| 4,783,221 | 11/1988 | Grove | 106/18.22 |

OTHER PUBLICATIONS

"Kathon 886: MW Microbicide & Kathon 893 MW Fungicide: Analysis in Metal Working Fluids by High Performance Liquid Chromatography" 1988, RandH Co.

*Primary Examiner*—Nicholas S. Rizzo
*Attorney, Agent, or Firm*—Michael B. Fein

[57] ABSTRACT

A composition comprising:
(a) A 3-isothiazolone compound
(b) a stabilizing amount of a metal salt, said metal salts selected from the group where the cation is copper, zinc, manganese, ferrous or ferric, and the anion is selected from the group consisting of an organic carboxylic acid of at least of six carbon atoms, EDTA, 8-hydroxyquinolinate, gluconate, o-phenanthroline, quinolinate, N,N-bis(2-hydroxy-5-sulfobenzyl) glycine, lignosulfonate polymers, and polyacrylates; and
(c) a locus to be protected against the growth of algae, bacteria, or fungi, selected from the group consisting of:
  (i) a metal working fluid (MWF) comprising at least one component selected from the group consisting of an alkanolamine, a petroleum sulfonate emulsifier, a boric acid ester or boric acid amide, a corrosion inhibitor, and a fatty acid;
  (ii) cooling tower water comprising corrosion inhibitors or scale inhibitors,
  (iii) laundry dish water;
  (iv) a cosmetic formulation;
  (v) a fuel system;
  (vi) an emulsion;
  (vii) a solid protective or decorative film.

11 Claims, No Drawings

STABILIZED METAL SALT/3-ISOTHIAZOLONE COMBINATIONS

This application is a continuation of application Ser. No. 426,144, filed Oct. 24, 1989 now abandoned.

BACKGROUND OF THE INVENTION

1. Field of the Invention

This invention relates to the stabilization of isothiazolones with various metal salts.

2. Description of the Prior Art

The use of 3-isothiazolones to control microbial growth in a variety of industrial environments (metal working fluids, cooling tower water, emulsions, plastic film, and the like) has been enhanced by the addition of stabilizers to maintain antimicrobial activity for longer periods of time; typical stabilizer systems include metal nitrates and the like.

U.S. Pat. Nos. 3,870,795 and 4,067,878 teach the stabilization of isothiazolones against chemical decomposition by addition of a metal nitrite or metal nitrate salts, but teach that other common metal salts, including carbonates, sulfates, chlorates, perchlorates, and chlorides are not as effective as nitrates or nitrites in stabilizing solutions of isothiazolones, such solutions usually being in water or in an hydroxylic solvent and immiscible with solvent-soluble isothiazolones. Salts or organic carboxylic acids of more than six carbon atoms with copper are not taught or considered in these patents.

U.S. Pat. Nos. 4,150,026 and 4,241,214 teach metal salt complexes of isothiazolones useful because of their enhanced thermal stability, while retaining biological activity. The metal salts listed do not include copper or zinc salts of organic carboxylic acids of six or more carbon atoms, or complexes of copper with organic-soluble reagents or polymers.

U.S. Pat. No. 4,608,183 teaches synergistic biocidal mixtures of isothiazolones and a metal complex with polyfunctional ligand, where the metal complex itself may be a biocide. Illustrated specifically is the water-soluble monocopper sodium citrate. It is known to use certain organic stabilizers for isothiazolones, generally for use situations where metal salts may create problems, such as corrosion, coagulation of latices, insolubility in non-aqueous media, interaction with the substrate to be stabilized, and the like.

Formaldehyde or formaldehyde-releasing chemicals are known stabilizers (see U.S. Pat. Nos. 4,165,318 and 4,129,448).

In certain applications, however, it is desirable to avoid addition of organic stabilizers by virtue of their volatility, decomposition under high heat, higher cost, difficulty in handling, potential toxicity, and the like. Formaldehyde is a suspected carcinogen, and it is desirable to reduce the use of formaldehyde or formaldehyde releasing chemicals in applications where contact with human skin or lungs may occur.

Grove, U.S. Pat. No. 4,783,221 teaches blends of the isothiazolones of the present invention with at least one metal salt of an organic carboxylic acid of at least six carbon atoms, wherein the metal is a transition metal, zinc, mercury, antimony, or lead, and also with a solvent diluent. The patent is directed to wood preservative compositions and does not teach or suggest use in metalworking fluids, cooling tower water, and the like. Further, Grove does not teach of enhanced stability of these compositions.

SUMMARY OF THE INVENTION

It has become an object of the invention to provide a stabilization system for isothiazolones which overcomes some or all of the disadvantages of prior art systems. It is also an object to provide a stabilized isothiazolone formulation which uses low levels of stabilizer so as to avoid interference with other components in systems in which isothiazolones are used as microbicides.

DETAILED DESCRIPTION OF THE INVENTION AND THE PREFERRED EMBODIMENTS

This invention comprises a composition comprising:

a) A 3-isothiazolone compound of the formula:

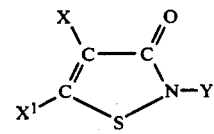

wherein Y is an alkyl or substituted alkyl of 1 to 18 carbon atoms; an unsubstituted or halogen substituted alkenyl or alkynyl of 2 to 8 carbon atoms; a cycloalkyl or substituted cycloalkyl of 3 to 12 carbon atoms; an aralkyl or halogen-, lower alkyl-, or lower alkoxy-substituted aralkyl of up to 10 carbon atoms; or an aryl or halogen-, lower alkyl-, or lower alkoxy-substituted aryl of up to 10 carbon atoms; and X and $X^1$ are hydrogen, halogen, or a $(C_1-C_4)$alkyl;

b) a stabilizing amount of a metal salt, said metal salts selected from the group where the cation is copper, zinc, manganese, ferrous or ferric, and the anion is selected from the group consisting of an organic carboxylic acid of at least six carbon atoms, ethylenediaminetetraacetate (EDTA), 8-hydroxyquinolinate, gluconate, o-phenanthroline, quinolinate, N,N-bis(2-hydroxy-5-sulfobenzyl) glycine, lignosulfonate polymers, and polyacrylates; and c) a locus to be protected against the growth of algae, bacteria, or fungi, selected from the group consisting of:
  (i) a metal working fluid (MWF) comprising at least one component selected from the group consisting of an alkanolamine, a petroleum sulfonate emulsifier, a boric acid ester or boric acid amide, a corrosion inhibitor, and a fatty acid;
  (ii) cooling tower water comprising corrosion inhibitors or scale inhibitors;
  (iii) laundry rinse water;
  (iv) a cosmetic formulation;
  (v) a fuel system;
  (vi) an emulsion;
  (vii) a solid protective or decorative film.

The 3-isothiazolones of interest include those disclosed in U.S. Pat. Nos. 3,523,121 and 3,761,488 as represented by the following formula:

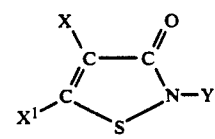

wherein Y is an alkyl or substituted alkyl of 1 to 18 carbon atoms, preferably from 4 to 10 carbon atoms; an unsubstituted or halogen substituted alkenyl or alkynyl of 2 to 8 carbon atoms, preferably from 2 to 4 carbon atoms; a cycloalkyl or substituted cycloalkyl of 3 to 12 carbon atoms, preferably from 5 to 8 carbon atoms; an aralkyl or halogen-, lower alkyl-, or lower alkoxy-substituted aralkyl of up to 10 carbon atoms; or an aryl or halogen-, lower alkyl-, or lower alkoxy-substituted aryl of up to 10 carbon atoms; and X and $X^1$ are hydrogen, halogen, or a ($C_1$–$C_4$) alkyl.

Representative Y substitutents include methyl, ethyl, propyl, isopropyl, butyl, hexyl, octyl, cyclohexyl, benzyl, 3,4-dichlorophenyl, 4-methoxybenzyl, 4-chlorobenzyl, 3,4-dichlorophenyl, 4-methoxyphenyl, 4-chlorophenyl, phenethyl, 2-(4-chlorophenyl)ethyl, hydroxymethyl, chloromethyl, chloropropyl, hydrogen, and the like.

Where the expression "lower" is employed in conjunction with terms, such as alkyl, alkoxy, etc., it is intended to indicate that the alkyl or alkyl portion thereof has 1 to 4 carbon atoms.

By a substituted alkyl group is meant an alkyl group having one or more of its hydrogen atoms replaced by another substituent group. Examples of the substituted alkyl groups which characterize 3-isothiaozlones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, halolkenyl, alkynyl, haloalkynyl, isothiazolonylalkyl, and the like.

By a substituted aralkyl group is meant an aralkyl group having one or more of the hydrogen atoms on either the aryl ring or the alkyl chain replaced by another substituent group. Examples of the substituent aralkyl groups which characterize 3-isothiaozlones of this invention include halogen-, lower alkyl-, or lower alkoxy-substituted aralkyl groups, and the like.

By a substituted aryl group is meant an aryl group, such as benzene, naphthalene, or pyridine, having one or more of the hydrogen atoms on the aryl ring replaced by another substitutent group. Examples of such substitutent groups include halogen, nitro, lower alkyl, lower alkyl-acrylamino, lower carbalkoxy, sufamyl, and the like.

Preferred isothiaozlones are 5-chloro-2-methyl-3-isothiazolone, 2-methyl-3-isothiazolone, 2-n-octyl-3-isothiazolone, and 4,5-dichloro-2-octyl-3-isothiazolone. It has been found that some chlorinated isothiazolones are not stabilized by the metal salt compounds used in this invention.

An important area requiring protection against microbial growth is metal working fluids (MWF). Metal working fluids are proprietary combinations of chemicals, which may contain such ingredients as are listed, but are not limited to such: alkanolamines, petroleum sulfonate surfactants, oils (naphthenic, paraffinic, etc.), chlorinated paraffins and fatty esters, sulfurized fatty compounds, phosphate esters, fatty acids and their amine salts, glycols, polyglycols, boric acid esters and amides. They are sold as concentrates to be diluted in use to 1–10% ingredients in water. They are utilized in the milling, machining, drilling, and other processing technologies for fabricating metal for the purposes of lubricating, cooling, preventing surface corrosion, and the like. Because metal working fluids are recycled and stored, the growth of microorganisms is favored. Isothiazolones have been found effective in preventing the growth of such organisms. Certain of the components in the metal working fluids will tend to destroy the isothiazolone and so remove its biocidal protective activity, so that stabilizers for the isothiazolone against such degradation are desirable. It is known in the art that the performance of biocides can occasionally be synergistically enhanced by combination with one or more other biocides, although such synergism is not readily predictable. There may also be other reasons, such as cost, solubility, protection against more than one degradative species, and the like, to combine two biocides even in the absence of synergism.

Among the stabilizing compounds useful in the compositions of this invention are salts of organic carboxylic acids which are water soluble or water dispersible. Preferred compounds are zinc octoate ("octoate" is a commonly used term which is equivalent to 2-ethylhexanoate) and copper alkanoate (mixture of about ($C_7$–$C_{13}$)alkyl carboxylates). Others which are suitable are zinc hexanoate, heptanoate, decanoate, dodecanoate, dodecenoate, cyclohexylcarboxylate, tetrahydrobenzoate, naphthenate, neodecanoate, oleate, benzoate, salts of disproportionated rosin acid (abietic, primaric acids), 2-phenylethanoate and the like.

Solvents may be used to dissolve the isothiazolones and may be any organic solvent which dissolves the isothiazolones, is compatible with the proposed end use, does not destabilize the isothiazolone, and does not react with the metal salt to eliminate its stabilizing action. Hydroxylic solvents, for example, polyols, such as glycols, monoethers of glycols, alcohols, and the like, may be used. An hydroxylic coalescent, such as trimethyl-1,3-pentanediol monoisobutyrate also may be used. Trimethyl-1,3-pentanediol monoisobutyrate is the designation Eastman Chemical uses for Texanol. In certain formulations, hydrocarbons, either aliphatic or aromatic, are useful solvents. Typical solvents are propylene glycol, dipropylene glycol monoethyl ether, xylene, mineral spirits, and the like. Solvents may be used in admixture as long as the metal salt remains soluble or is well dispersed enough so as to be added conveniently and uniformly to the test formulation.

The amounts of stabilizing metal salt compounds employed will vary depending on use conditions and concentrations of the isothiazolone in the mixture. In more concentrated solutions, effective amounts of metal salt based on isothiazolone are in the ratios of from about 1:50 to about 50:1. Obviously higher amounts may be used, but at additional cost. At high levels of dilution of the isothiazolone (such as from about 0.1 ppm to about 10 percent isothiazolone in the solvent), the ratio of stabilizer to isothiazolone can range from about 1:7 to about 50:1. The stabilization advantages of the metal salts are noted even when the isothiazolone contains other salt stabilizers such as those set forth in U.S. Pat. Nos. 3,870,795; 4,067,878; 4,150,026 and 4,241,214.

Other known biocides may be combined advantageously with the stabilized isothiazolones of this invention.

The following examples will further illustrate this invention, but are not intended to limit it in any way. All parts and percentages are by weight and all temperatures in degrees Centigrade, unless otherwise stated. Methods for quantitative determination of the isothiazolones in the following examples are described in detail in "Kathon 886 MW Microbicide and Kathon 893 MW Fungicide: Analysis in Metal Working Fluids by High-Performance Liquid Chromatography," 1988, Rohm and Haas Company.

EXAMPLE 1

Stability Study

This example demonstrates the stabilizing effect of metal salts for isothiazolones added to several different metal working fluids (MWF). MWF concentrates A through C were "semi-synthetic" types having about 10 to 15% naphthenic/paraffinic oil, about 50% water, about 15% emulsifying agents, and about 15% of pH adjusting amines, anticorrosive agents, and EP (extreme pressure) agents. MWF concentrate D was a synthetic type having about 70% water, 15% long chain non-ionic surfactants or esters, 15% phosphate or amine carboxylate corrosion inhibitor, pH adjusting amines, and EP agents. MWF concentrate E was a soluble type having about 50 to 75% naphthenic/paraffinic oil, about 10-20% emulsifying agents, and about 15% pH adjusting amines, anticorrosive agents and EP agents.

The test method is as follows: Into a glass vial in the following order were placed: a) 5 parts by weight of the metal working fluid (MWF) concentrate diluted in water, b) 5 parts of the stabilizer in solution or dispersion, c) 5 parts water, d) 5 parts of an aqueous solution containing 80 ppm active ingredient (a.i.), prepared by dilution of a 14.4% aqueous solution of an approximately 75/25 mixture (designated IT-MIX) of 5-chloro-2-methyl-3-isothiazolone and 2-methyl-3-isothiazolone, the former being considered the active ingredient for these purposes; also present was 9.2 weight percent magnesium chloride and 15.7% magnesium nitrate. Thus the final mixture contained 3-5% of the MWF, 20 ppm active ingredient of the isothiazolone, and 0 (control) to 40 ppm of the stabilizer. The vials were then capped, stored at ambient room temperature in a closed cabinet for a designated time, filtered through a 0.45 micron filter into another vial and analyzed the same day. The relative concentration of the active ingredient was determined by reverse phase high pressure liquid chromatography.

Cupric alkanoate is supplied as a 10% solution in xylene. Copper 8-hydroxyquinolinate and copper o-phenanthroline are prepared in situ by adding 20 ppm of copper as cupric sulfate and a 50-fold excess of the organic component. Lignosulfonate polymers (Marasperse N22 from Reed Lignin Co., Reax 88A from Westvaco Chemical Division) are used as dispersants. The lignosulfonate combinations were formed by mixing a solution of 1% copper or zinc (as the sulfate) and 9% polymer in water, mixing overnight, and diluting with water.

TABLE 1

COMPARISON OF SEVERAL COPPER AND ZINC SALTS IN FOUR MWF SYSTEMS AFTER THREE DAYS AT ROOM TEMPERATURE

| Stabilizer | Stabilizer level (ppm) | % AI remaining | | | |
|---|---|---|---|---|---|
| | | MWF-A | MWF-B | MWF-C | MWF-D |
| None | 0 | 43 | 0 | 8 | 55 |
| Cu Alkanoate | 20 | 59 | 89 | 97 | 67 |
| Cu 8-hydroxyquinolinate | 20 | 68 | 78 | 92 | 65 |
| Cu o-phenanthroline | 20 | 73 | 79 | 92 | 73 |
| Cu Marasperse N22 | 20 | 76 | 76 | 98 | 66 |
| Cu Reax 88A | 20 | 71 | 75 | 100 | 75 |
| Zn Marasperse N22 | 100 | 69 | 45 | — | — |
| Zn Reax 88A | 100 | 73 | 53 | — | — |
| Zn Octoate | 100 | 76 | 63 | — | — |

Original system contained 15 ppm 5-chloro-2-methyl-3-isothiazolone (AI) with 3% MWF concentrate A, or 5% MWF concentrate B, or 4% MWF concentrate C, or 4% MWF concentrate D.

EXAMPLE 2

Stability Study

This example demonstrates the stabilizing effect of copper gluconate and ferric EDTA in a soluble metal-working fluid. These particular stability studies were run in conjunction with antimicrobial activity studies similar to those described in Examples 3 through 8. during the antimicrobial activity studies aliquots of the MWF were removed periodically and evaluated for isothiazolone concentration via HPLC analysis using reverse phase gradient separation on an octadecylsilane column with an UV detector.

TABLE 2

Comparison of Two Metal Salts in MWF-E

| Metal Salt | ppm AI | ppm Copper/Iron | % AI remaining | | |
|---|---|---|---|---|---|
| | | | 1 week | 2 weeks | 4 weeks |
| Copper Gluconate | 7.5 | 0 | 13 | <7 | <7 |
| " | 7.5 | 20 | 44 | 27 | 13 |
| " | 15 | 0 | 9 | <3 | <3 |
| " | 15 | 20 | 47 | 31 | 12 |
| Ferric EDTA | 15 | 0 | 9 | <3 | <3 |
| " | 15 | 40 | 46 | 30 | 7 |
| " | 15 | 80 | 59 | 45 | 13 |

EXAMPLES 3-8

Antimicrobial Activity Studies

The preservation of metalworking fluid use dilutions was determined in the laboratory using a test method designed to simulate some of the important conditions which exist in the field, such as frequent recontamination of the fluid with microorganisms, the presence of organic nutrients which can stimulate microbial growth, and the presence of metal chips and fines. However, since the conditions of use of metal working fluids in the field vary extensively, the actual time span that a preservative remains effective under the conditions of this laboratory test will not always be the same as that experienced in the field. Nevertheless, the test does provide a good indication of differences in the persistence of various treatments and these differences would be expected to be seen in the field.

Fifty milliliter samples of the most commonly recommended use dilution of the metal working fluids under test were dosed with appropriate concentrations of the antimicrobials being evaluated. One sample representing each fluid was left undosed to serve as a positive control. Between 0.5 and 1 gram of appropriate metal fines was added to each test sample to simulate the presence of "swarf"; swarf refers to the metal fines and shavings (from drilling, grinding, and similar operations) which are removed during metal-working operations. Each of these test samples was then challenged with one and one-half milliliters of a heavy inoculum of bacterial and fungal microorganisms to provide a final concentration in the test samples of 1,000,000 to 10,000,000 microorganisms per ml of metalworking fluid. These microorganisms were isolated from naturally contaminated metalworking fluids of various types and were maintained in a mixture of several untreated (no antimicrobial) metalworking fluids to which fresh fluid was added weekly.

The test samples were stored at ambient temperature for a total of four weeks during which time they were reinoculated weekly as described above. To estimate the number of microorganisms present in the test samples during the test, agar plate counts were made, usually one week following each inoculation, just prior to reinoculation. The agar plates were incubated at 86° F. (30° C.) for seven days and then observed for the number of colony forming units (cfu) present on each plate.

Examples 3 through 8 demonstrate enhanced biological control of microbial growth by several metal salts with isothiazolone in MWF-A. Experiments were run as described above.

TABLE 3

Effect of Copper Gluconate on IT-MIX in Semi-Synthetic Fluid A

| ppm A.I. | ppm Copper | No. of Microbial C.F.U./ml of Test Sample |  |  |  |
|---|---|---|---|---|---|
|  |  | 1 week | 2 weeks | 3 weeks | 4 weeks |
| 0 | 0 | >$10^6$ | >$10^6$ | >$10^6$ | >$10^6$ |
| 20 | 0 | >$10^6$ | >$10^6$ | >$10^6$ | >$10^6$ |
| 20 | 5 | <$10^3$ | >$10^6$ | >$10^6$ | >$10^6$ |
| 20 | 10 | <$10^3$ | <$10^3$ | $10^5$ | >$10^6$ |
| 20 | 20 | <$10^3$ | <$10^3$ | <$10^3$ | <$10^3$ |
| 0 | 5 | >$10^6$ | >$10^6$ | >$10^6$ | >$10^6$ |
| 0 | 10 | >$10^6$ | >$10^6$ | >$10^6$ | >$10^6$ |
| 0 | 20 | >$10^6$ | >$10^6$ | >$10^6$ | >$10^6$ |

Inocula
Zero Time — 1,125,000,000 c.f.u/ml.
Week 1 — 1,650,000,000 c.f.u/ml.
Week 2 — 2,025,000,000 c.f.u/ml.
Week 3 — 1,865,000,000 c.f.u/ml.

TABLE 4

Effect of Zinc Gluconate on IT-MIX in Semi-Synthetic Fluid A

| ppm A.I. | ppm Zinc | No. of Microbial C.F.U./ml of Test Sample |  |  |  |
|---|---|---|---|---|---|
|  |  | 1 week | 2 weeks | 3 weeks | 4 weeks |
| 0 | 0 | >$10^6$ | >$10^6$ | >$10^6$ | >$10^6$ |
| 20 | 0 | <$10^3$ | >$10^6$ | >$10^6$ | >$10^6$ |
| 20 | 20 | <$10^3$ | >$10^6$ | >$10^6$ | >$10^6$ |
| 20 | 40 | <$10^3$ | >$10^6$ | >$10^6$ | >$10^6$ |
| 20 | 80 | <$10^3$ | <$10^3$ | >$10^6$ | >$10^6$ |
| 20 | 100 | <$10^3$ | <$10^3$ | >$10^6$ | >$10^6$ |

TABLE 4-continued

Effect of Zinc Gluconate on IT-MIX in Semi-Synthetic Fluid A

| ppm A.I. | ppm Zinc | No. of Microbial C.F.U/ml of Test Sample |  |  |  |
|---|---|---|---|---|---|
|  |  | 1 week | 2 weeks | 3 weeks | 4 weeks |
| 20 | 200 | <$10^3$ | <$10^3$ | <$10^3$ | <$10^3$ |
| 20 | 300 | <$10^3$ | <$10^3$ | <$10^3$ | <$10^3$ |
| 0 | 20 | >$10^6$ | >$10^6$ | >$10^6$ | >$10^6$ |
| 0 | 80 | >$10^6$ | >$10^6$ | >$10^6$ | >$10^6$ |
| 0 | 100 | >$10^6$ | >$10^6$ | >$10^6$ | >$10^6$ |
| 0 | 300 | >$10^6$ | >$10^6$ | >$10^6$ | >$10^6$ |

Inocula
Zero Time — 1,590,000,000 c.f.u.
Week 1 — 2,950,000,000 c.f.u.
Week 2 — 1,560,000,000 c.f.u.
Week 3 — 1,430,000,000 c.f.u.

TABLE 5

Effect of Ferric N,N-Bis(2-hydroxy-5-sulfobenzyl) glycine on IT-MIX in Semi-Synthetic Fluid A

| ppm A.I. | ppm Iron | No. of Microbial C.F.U./ml of Test Sample |  |  |  |
|---|---|---|---|---|---|
|  |  | 1 week | 2 weeks | 3 weeks | 4 weeks |
| 0 | 0 | >$10^6$ | >$10^6$ | >$10^6$ | >$10^6$ |
| 7 | 0 | $10^6$ | >$10^6$ | >$10^6$ | >$10^6$ |
| 7 | 200 | — | $10^4$ | $10^3$ | $10^3$ |
| 7 | 500 | — | <$10^3$ | <$10^3$ | <$10^3$ |
| 0 | 200 | — | >$10^6$ | >$10^6$ | >$10^6$ |
| 0 | 500 | — | >$10^6$ | >$10^6$ | >$10^6$ |

TABLE 6

Effect of Ferric EDTA on IT-MIX in Semi-Synthetic Fluid A

| ppm A.I. | ppm Iron | No. of Microbial C.F.U./ml of Test Sample |  |  |  |
|---|---|---|---|---|---|
|  |  | 1 week | 2 weeks | 3 weeks | 4 weeks |
| 0 | 0 | >$10^6$ | >$10^6$ | >$10^6$ | >$10^6$ |
| 7 | 0 | >$10^6$ | $10^5$ | >$10^6$ | >$10^6$ |
| 7 | 25 | $10^4$ | $10^3$ | <$10^3$ | <$10^3$ |
| 7 | 50 | $10^3$ | $10^3$ | <$10^3$ | <$10^3$ |
| 7 | 100 | $10^3$ | <$10^3$ | <$10^3$ | <$10^3$ |
| 7 | 200 | $10^3$ | <$10^3$ | <$10^3$ | <$10^3$ |
| 0 | 200 | >$10^6$ | >$10^6$ | >$10^6$ | >$10^6$ |

TABLE 7

Effect of Zinc EDTA on IT-MIX in Semi-Synthetic Fluid A

| ppm A.I. | ppm Zinc | No. of Microbial C.F.U./ml of Test Sample |  |  |  |
|---|---|---|---|---|---|
|  |  | 1 week | 2 weeks | 3 weeks | 4 weeks |
| 0 | 0 | >$10^6$ | >$10^6$ | >$10^6$ | >$10^6$ |
| 7 | 0 | >$10^6$ | >$10^6$ | >$10^6$ | >$10^6$ |
| 7 | 200 | >$10^6$ | >$10^6$ | >$10^6$ | >$10^6$ |
| 7 | 500 | <$10^3$ | <$10^3$ | >$10^6$ | >$10^6$ |
| 0 | 200 | >$10^6$ | >$10^6$ | >$10^6$ | >$10^6$ |
| 0 | 500 | >$10^6$ | >$10^6$ | >$10^6$ | >$10^6$ |

TABLE 8

Effect of Manganese EDTA on IT-MIX in Semi-Synthetic Fluid A

| ppm A.I. | ppm Manganese | No. of Microbial C.F.U./ml of Test Sample |  |  |  |
|---|---|---|---|---|---|
|  |  | 1 week | 2 weeks | 3 weeks | 4 weeks |
| 0 | 0 | >$10^6$ | >$10^6$ | >$10^6$ | >$10^6$ |
| 7 | 0 | >$10^6$ | >$10^6$ | >$10^6$ | >$10^6$ |
| 7 | 200 | — | $10^4$ | $10^5$ | >$10^6$ |
| 7 | 500 | — | <$10^3$ | <$10^3$ | >$10^6$ |
| 0 | 200 | — | >$10^6$ | >$10^6$ | >$10^6$ |
| 0 | 500 | — | >$10^6$ | >$10^6$ | >$10^6$ |

What is claimed is:
1. A composition comprising:

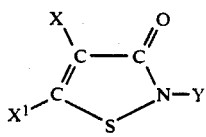

(a) A 3-isothiazolone compound of the formula: wherein Y is an alkyl or substituted alkyl of 1 to 18 carbon atoms; an unsubstituted or halogen substituted alkenyl or alkynyl of 2 to 8 carbon atoms; a cycloalkyl or substituted cycloalkyl of 3 to 12 carbon atoms; an aralkyl or halogen-, lower alkyl-, or lower alkoxy-substituted aralkyl of up to 10 carbon atoms; or an aryl or halogen-, lower alkyl-, or lower alkoxy-substituted aryl of up to 10 carbon atoms; and X and $X^1$ are hydrogen, halogen, or a ($C_1$-$C_4$) alkyl;

(b) a stabilizing amount of a metal salt, said metal salts selected from the group where the cation is copper, zinc, manganese, ferrous or ferric, and the anion is selected from the group consisting of EDTA, 8-hydroxyquinolinate, gluconate, o-phenanthroline, quinolinate, N,N-bis(2-hydroxy-5-sulfobenzyl) glycine, lignosulfonate polymers, and polyacrylates; and (c) a locus to be protected against the growth of algae, bacteria, or fungus consisting of a metal working fluid (MWF) comprising at least one component selected from the group consisting of an alkanolamine, a petroleum sulfonate emulsifier, a boric acid ester or boric acid amide, a corrosion inhibitor, and a fatty acid.

2. An MWF composition according to claim 1 which comprises from about 0.01 parts per million to about 4 parts per hundred of said 3-isothiazolone compound, based on composition.

3. An MWF composition according to claim 2 which comprises from about 0.01 parts per million to about 10 parts per hundred of metal salt.

4. The composition of claim 3 which comprises from about 1 to 2000 ppm of said 3-isothiazolone, from about 0.1 ppm to 2 pph of said metal salt.

5. An MWF compositions according to claim 1 further including the solvent selected from the group consisting of aliphatic hydrocarbon, aromatic hydrocarbon, dihydric alcohol and monoalkyl ethers of dihydric alcohols.

6. The composition of claim 1 wherein the salt is zinc octoate.

7. The composition of claim 1 wherein Y is ($C_1$-$C_{18}$) alkyl, ($C_3$-$C_{12}$) cycloalkyl, ($C_7$-$C_{10}$) aralkyl, or ($C_7$-$C_{10}$) ring-chlorinated aralkyl; X is hydrogen, methyl or chloro; and $X^1$ is hydrogen or chloro.

8. The composition of claim 7 wherein said 3-isothiazolone is selected from 4,5-dichloro-2-octyl-3-isothiazolone, 2-octyl-3-isothiazolone, 5-chloro-2-methyl-3-isothiazolone and 2-methyl-3-isothiazolone.

9. A method for inhibiting the growth of bacteria, fungi, or algae in a locus consisting of a metal working fluid (MWF) comprising at least one component selected from the group consisting of an alkanolamine, a petroleum sulfonate emulsifier, a boric acid ester or boric acid amide, a corrosion inhibitor, and a fatty acid; comprising incorporating into said locus, in an amount which is effective to adversely affect the growth of bacteria, fungi, or algae, a composition comprising (1) a 3-isothiazolone compound of the formula:

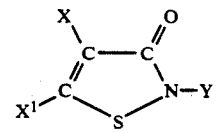

wherein Y is an alkyl or substituted alkyl of 1 to 18 carbon atoms; an unsubstituted or halogen substituted alkenyl or alkynyl of 2 to 8 carbon atoms; a cycloalkyl or substituted cycloalkyl of 3 to 12 carbon atoms; an aralkyl or halogen-, lower alkyl-, or lower alkoxy-substituted aralkyl of up to 10 carbon atoms; or an aryl or halogen-, lower alkyl-, or lower alkoxy-substituted aryl of up to 10 carbon atoms; and X and $X^1$ are hydrogen, halogen, or a ($C_1$-$C_4$) alkyl; and (2) a stabilizing amount of a metal salt wherein the cation is selected from the group consisting of copper, zinc, manganese, ferrous or ferric, and wherein the anion is selected from the group consisting of EDTA, 8-hydroxyquinolinate, gluconate, o-phenanthroline, quinolinate, N,N-bis(2-hydroxy-5-sulfobenzyl) glycine, lignosulfonate polymers, and polyacrylates.

10. A method for stabilizing an isothiazolone comprising use of an amount of a metal salt where the cation is selected from the group consisting of copper, zinc, manganese, ferrous or ferric, and the anion is selected from the group consisting of an organic carboxylic acid of at least six carbon atoms, EDTA, 8-hydroxyquinolinate, gluconate, o-phenanthroline, quinolinate, N,N-bis(2-hydroxy-5-sulfobenzyl) glycine, lignosulfonate polymers, and polycarbonates, sufficient to stabilize said isothiazolone.

11. The method according to claim 10, wherein the isothiazolone is in a locus consisting of a metal working fluid (MWF) comprising at least one component selected from the group consisting of an alkanolamine, a petroleum sulfonate emulsifier, a boric acid ester or boric acid amide, a corrosion inhibitor, and a fatty acid.

* * * * *